United States Patent
Kiyose

(10) Patent No.: US 10,653,390 B2
(45) Date of Patent: May 19, 2020

(54) ULTRASONIC DEVICE, ULTRASONIC PROBE, ELECTRONIC APPARATUS, AND METHOD FOR MANUFACTURING ULTRASONIC DEVICE

(71) Applicant: SEIKO EPSON CORPORATION, Tokyo (JP)

(72) Inventor: Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 1438 days.

(21) Appl. No.: 14/582,635

(22) Filed: Dec. 24, 2014

(65) Prior Publication Data

US 2015/0190118 A1 Jul. 9, 2015

(30) Foreign Application Priority Data

Jan. 6, 2014 (JP) .................................. 2014-000132

(51) Int. Cl.
*A61B 8/00* (2006.01)
*G10K 11/00* (2006.01)
*A61B 8/14* (2006.01)
*A61B 8/08* (2006.01)

(52) U.S. Cl.
CPC .......... *A61B 8/4483* (2013.01); *A61B 8/4411* (2013.01); *A61B 8/4427* (2013.01); *A61B 8/4444* (2013.01); *A61B 8/4494* (2013.01); *G10K 11/002* (2013.01); *A61B 8/14* (2013.01); *A61B 8/4281* (2013.01);
(Continued)

(58) Field of Classification Search
CPC ... G10K 11/002; A61B 8/4483; A61B 8/4411; A61B 8/4427; A61B 8/4494; A61B 8/4444; A61B 8/4455; A61B 8/467; A61B 8/4281; A61B 8/461; A61B 8/5207; A61B 8/14

See application file for complete search history.

(56) References Cited

U.S. PATENT DOCUMENTS 4,507,582 A * 3/1985 Glenn .................... G10K 11/02
310/327
2002/0156373 A1* 10/2002 Wakabayashi ........ B06B 1/0622
600/437
(Continued)

FOREIGN PATENT DOCUMENTS

JP 2002-034098 A 1/2002
JP 2010-022931 A 2/2010
(Continued)

*Primary Examiner* — Pascal M Bui Pho
*Assistant Examiner* — Farouk A Bruce
(74) *Attorney, Agent, or Firm* — Global IP Counselors, LLP

(57) ABSTRACT

An ultrasonic device includes: a substrate on which ultrasonic elements configured to transmit and receive ultrasound and a cable electrically connected to the ultrasonic elements are installed; an acoustic lens having a plurality of projecting portions connected to one of the substrate and the cable; and an acoustic matching unit located between the substrate and the acoustic lens, wherein the projecting portions extend along an outer perimeter of the substrate, and the projecting portions are provided at a lower ratio per unit length in a direction in which the projecting portions extend in a place where the cable is installed than in a place where the cable is not installed.

18 Claims, 9 Drawing Sheets

(52) U.S. Cl.
CPC ............ *A61B 8/4455* (2013.01); *A61B 8/461* (2013.01); *A61B 8/467* (2013.01); *A61B 8/5207* (2013.01)

(56) References Cited

U.S. PATENT DOCUMENTS

| | | | |
|---|---|---|---|
| 2007/0063616 A1* | 3/2007 | Adachi ................ | B06B 1/0622 310/311 |
| 2010/0013358 A1 | 1/2010 | Nakayama | |
| 2010/0036257 A1 | 2/2010 | Sano et al. | |
| 2010/0179430 A1* | 7/2010 | Sano .................... | B06B 1/0292 600/459 |
| 2014/0211587 A1 | 7/2014 | Kiyose | |

FOREIGN PATENT DOCUMENTS

| | | | | |
|---|---|---|---|---|
| JP | 2012100994 A * | 5/2012 | | |
| JP | 2014-146884 A | 8/2014 | | |
| JP | 2014-146885 A | 8/2014 | | |
| WO | 2008/056643 A1 | 5/2008 | | |
| WO | WO-2013046080 A1 * | 4/2013 | ............ | G10K 11/30 |

* cited by examiner

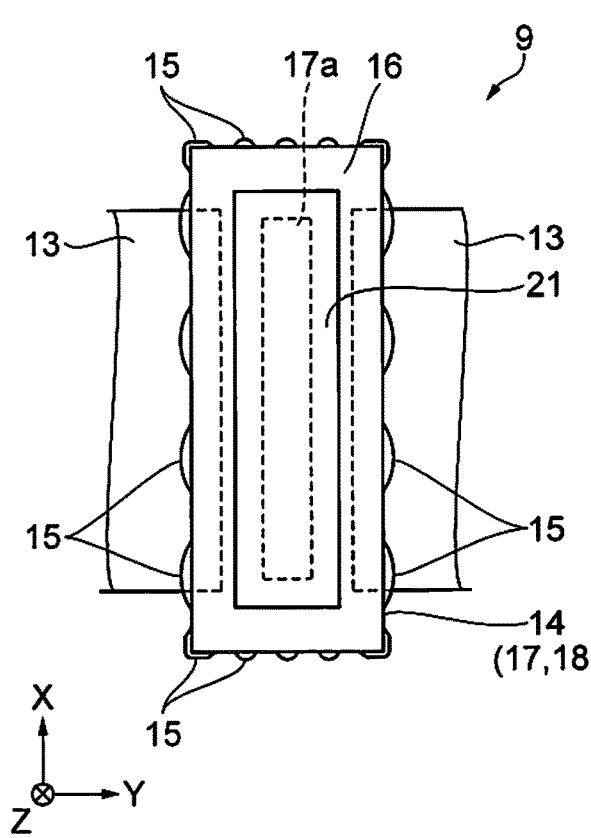
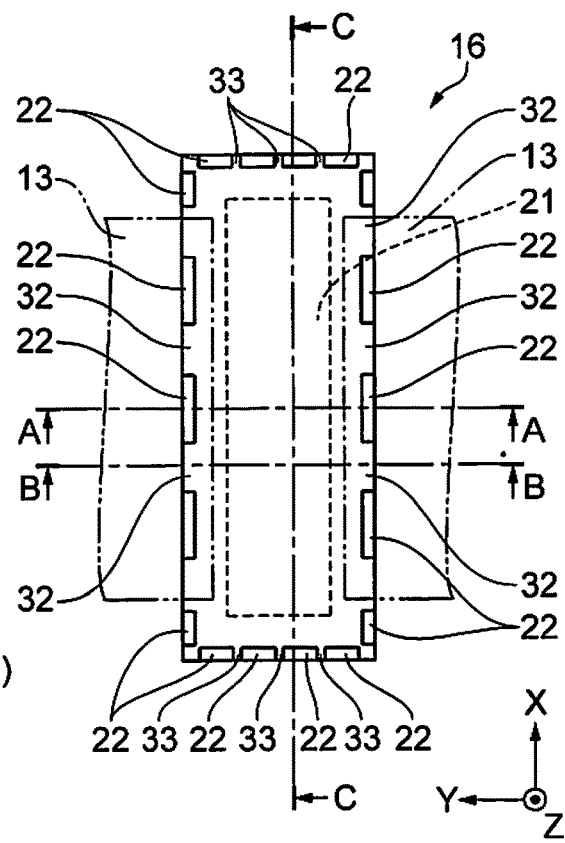
FIG. 5A    FIG. 5B
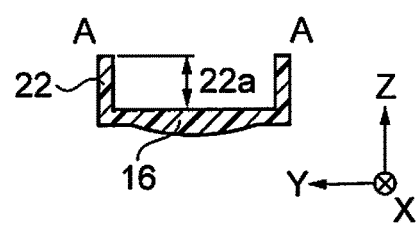
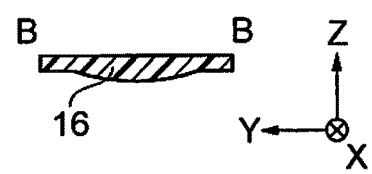
FIG. 5C    FIG. 5D
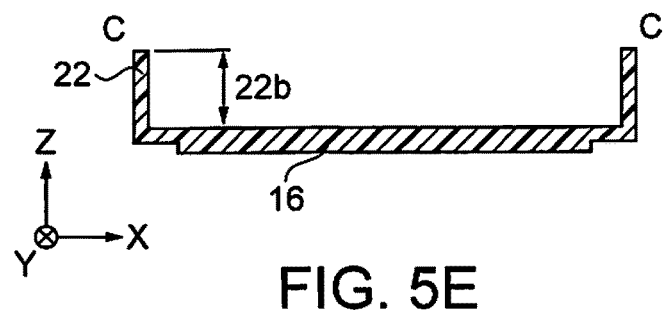
FIG. 5E

ULTRASONIC DEVICE, ULTRASONIC PROBE, ELECTRONIC APPARATUS, AND METHOD FOR MANUFACTURING ULTRASONIC DEVICE

BACKGROUND

1. Technical Field

The present invention relates to an ultrasonic device, an ultrasonic probe, an electronic apparatus, and a method for manufacturing an ultrasonic device.

2. Related Art

Ultrasonic devices using ultrasonic elements that transmit and receive ultrasound have been used in various applications. WO 2008/056643 A1, which is an example of related art, discloses an ultrasonic device including ultrasonic elements. This ultrasonic device includes an ultrasonic element array substrate having ultrasonic elements that transmit and receive ultrasound, and an acoustic lens that focuses the ultrasound.

The ultrasonic elements have a structure in which a space is formed between a membrane body on which a lower electrode is installed and a membrane body on which an upper electrode is installed. Further, an AC voltage is applied to the lower electrode and the upper electrode. This causes an electrostatic force to act between the membrane bodies, so that the membrane bodies vibrate and transmit ultrasound. The ultrasound passes through the acoustic lens, thereby being emitted so as to be focused on a predetermined place. The acoustic lens is formed using silicone resin, which is a material that easily transfers ultrasound to a material being examined.

The ultrasonic element array substrate is installed in a support member, and a flexible substrate is installed as a cable in the support member. The flexible substrate is connected to the electrodes of the ultrasonic elements by wire bonding. The periphery of wires is sealed by a resin. The acoustic lens and the ultrasonic element array substrate are bonded by an adhesive agent, and the adhesive agent is solidified to serve as a portion that matches the acoustic impedance. The adhesive agent is arranged also between the acoustic lens and the flexible substrate, thereby bonding the acoustic lens and the flexible substrate together.

When ultrasound is emitted from the acoustic lens to the material being examined, water or gel is arranged between the acoustic lens and the material being examined. This reduces reflection or attenuation of the ultrasound, thereby allowing the ultrasonic device to emit ultrasound efficiently from the acoustic lens to the material being examined. Accordingly, the ultrasonic device is used with the acoustic lens being in contact with moisture.

SUMMARY

In the ultrasonic device according to WO 2008/056643 A1, the resin is applied to the periphery of wires. The resin is installed to seal the wires. Further, the adhesive agent is applied, covering the ultrasonic element array substrate, the resin, and part of the flexible substrate. The acoustic lens is installed over the adhesive agent. The resin for sealing and the adhesive agent are applied and are covered by the acoustic lens. At this time, air bubbles may remain in the periphery of the electrodes of the flexible substrate in some cases. In such cases, the adhesive agent becomes thin in the places containing the air bubbles, where the moisture permeability is therefore increased. There is a risk of separation of the acoustic lens from the ultrasonic element array substrate, because the adhesiveness of the adhesive agent is weakened when the moisture enters. Further, there is a high risk of failure to drive the ultrasonic elements, because electrolytic corrosion of the electrodes of the flexible substrate occurs to cause a short circuit when the moisture enters. Therefore, there has been desire for ultrasonic devices in which the moisture permeability of the junction between the substrate on which the ultrasonic elements are installed and the cable can be reduced.

The invention has been devised to solve the aforementioned problems and can be practiced as embodiments or application examples described below.

APPLICATION EXAMPLE 1

An ultrasonic device according to this application example includes: a substrate on which ultrasonic elements configured to transmit and receive ultrasound and a cable electrically connected to the ultrasonic elements are installed; an acoustic lens having a plurality of projecting portions connected to one of the substrate and the cable; and an acoustic matching unit located between the substrate and the acoustic lens, wherein the projecting portions extend along an outer perimeter of the substrate, and the projecting portions are provided at a lower ratio per unit length in a direction in which the projecting portions extend in a place where the cable is installed than in a place where the cable is not installed.

According to this application example, the ultrasonic elements and the cable are installed on the substrate. Electricity is supplied to the ultrasonic elements through the cable, and ultrasound is transmitted from the ultrasonic elements. The acoustic matching unit and the acoustic lens are installed in layers on the substrate. The ultrasound transmitted from the ultrasonic elements passes through the acoustic matching unit and the acoustic lens, so as to be transmitted from the ultrasonic device.

In the acoustic lens, a plurality of projecting portions are installed along the outer perimeter of the substrate. The acoustic matching unit is formed by solidifying a resin or the like applied to the substrate while pressing the acoustic lens. When the resin is pressed with the acoustic lens, the resin deforms and spreads into a plate. At this time, the projecting portions define the thickness of the resin.

The projecting portions extend along the outer perimeter of the substrate. Some of the projecting portions are connected to the cable. Others of the projecting portions are connected to the substrate in the place where the cable is not installed. The projecting portions are provided at a lower ratio per unit length in the place where the cable is installed than in the place where the cable is not installed. Thus, the gaps between the projecting portions are larger in the place where the cable is present than in the place where the cable is not present. When the resin is sandwiched by the substrate and the acoustic lens, the resin flows out through the gaps between the projecting portions. Accordingly, the resin flows out more easily to the place where the cable is present than to the place where the cable is not present. When the resin flows out, air bubbles are pushed out, which enables the thickness of the resin to be ensured in the place where the cable is present. As a result, the acoustic matching unit, which is formed by solidification of the resin and has an appropriate thickness, covers the cable. Therefore, the moisture permeability of the junction between the substrate and the cable can be reduced.

APPLICATION EXAMPLE 2

In the ultrasonic device according to the above described application example, the projecting portions are provided at larger intervals in the place where the cable is installed than in the place where the cable is not installed.

According to this application example, the projecting portions are provided at larger intervals in the place where the cable is installed than in the place where the cable is not installed. When the projecting portions are provided at large intervals, the resin serving as the material for the acoustic matching unit flows easily. Accordingly, air bubbles can be allowed to flow out in the place where the cable is installed.

APPLICATION EXAMPLE 3

In the ultrasonic device according to the above described application example, in plan view as viewed in a thickness direction of the substrate, the projecting portions have a smaller length, in a direction along the outer perimeter of the substrate, at positions on an inner side than on the outer peripheral side of the substrate.

According to this application example, the length of the cross sections of the projecting portions is smaller on the inner side of the substrate than on the outer peripheral side thereof. The length of the cross sections means the length of the projecting portions in the direction along the outer perimeter of the substrate. This allows the gaps between the projecting portions to be longer on the inner side and shorter on the outer peripheral side. Thus, the fluid resistance of the resin passing through the gaps between the projecting portions can be reduced, thereby allowing the resin to swiftly flow out to the outside of the acoustic lens.

APPLICATION EXAMPLE 4

In the ultrasonic device according to the above described application example, the substrate has a first side and a second side that are opposed to each other, the cable is located at the first side and the second side, and openings between the projecting portions on the first side and openings between the projecting portions on the second side are alternatingly arranged.

According to this application example, the cable is located at the first side and the second side. Further, the openings between the projecting portions on the first side and the openings between the projecting portions on the second side are arranged alternatingly. In the case where the openings on the first side and the openings on the second side are located in places opposed to each other, lines connecting the opposed openings are parallel to each other. In that case, the acoustic lens easily bends along the parallel lines because there is less strength in places where the openings are present than in places where the projecting portions are present. On the other hand, when the openings are arranged alternatingly, lines connecting the openings on the first side and the openings on the second side intersect each other. Accordingly, the places where the acoustic lens easily bends extend along the intersecting lines, and therefore the acoustic lens can be made less likely to bend as compared to the case where the places susceptible to bending extend along parallel lines.

APPLICATION EXAMPLE 5

In the ultrasonic device according to the above described application example, the acoustic matching unit is partially located between the cable and the projecting portions.

According to this application example, the acoustic matching unit is partially located between the cable and the projecting portions. Thus, the cable is covered by the acoustic matching unit also between the cable and the projecting portions. Accordingly, the moisture permeability can be suppressed to a low level.

APPLICATION EXAMPLE 6

An ultrasonic probe according to this application example includes: the ultrasonic device according to any one of the aforementioned application examples; and a driving circuit configured to drive the ultrasonic device.

According to this application example, the ultrasonic probe includes the ultrasonic device described above and the driving circuit configured to drive the ultrasonic device. The ultrasonic probe of this application example includes the ultrasonic device in which the moisture permeability of the junction between the cable and the substrate is suppressed to a low level. Accordingly, a short circuit due to moisture is less likely to occur in the cable, which makes it possible to provide an ultrasonic probe configured to perform transmission and reception of ultrasound with high long-term reliability.

APPLICATION EXAMPLE 7

An electronic apparatus according to this application example includes: the ultrasonic device according to any one of the aforementioned application examples; a processing unit connected to the ultrasonic device, the processing unit being configured to generate an image using an output of the ultrasonic device; and a display unit configured to display the image.

According to this application example, the electronic apparatus includes the aforementioned ultrasonic device and the processing unit. The processing unit generates image data using the output of the ultrasonic device. The electronic apparatus of this application example includes the ultrasonic device in which the moisture permeability of the junction between the cable and the substrate is suppressed to a low level. Accordingly, a short circuit due to moisture is less likely to occur in the cable, which makes it possible to provide an electronic apparatus configured to perform transmission and reception of ultrasound with high long-term reliability.

APPLICATION EXAMPLE 8

A method for manufacturing an ultrasonic device according to this application example includes: arranging a resin at the center of a substrate, at an end of which a cable is installed; pressing the resin in a state of being sandwiched by the substrate and an acoustic lens having projecting portions; and forming an acoustic matching unit by solidification of the resin, wherein the projecting portions extend along an outer perimeter of the substrate, and the projecting portions are provided at a lower ratio per unit length in a direction in which the projecting portions extend in a place where the cable is installed than in a place where the cable is not installed.

According to this application example, the resin is arranged at the center of the substrate, at an end of which the cable is installed. The resin sandwiched by the substrate and the acoustic lens having the projecting portions is pressed. The projecting portions extend along the outer perimeter of the substrate. When the resin is pressed with the acoustic lens, the resin deforms and spreads into a plate. At this time, the projecting portions define the thickness of the resin. The projecting portions are provided at a lower ratio per unit length in the direction in which the projecting portions extend in the place where the cable is installed than in the place where the cable is not installed. Thus, the gaps are larger in the place where the cable is present than in the place where the cable is not present. When the resin is sandwiched by the substrate and the acoustic lens, the resin flows out through the gaps between the projecting portions. Accordingly, the resin is configured to flow out more easily into the place where the cable is present than into the place where the cable is not present. Therefore, the resin causes air bubbles to flow out to the place where the cable is present. As a result, the acoustic matching unit, which is formed by solidification of the resin and has an appropriate thickness, covers the cable, and thus the moisture permeability can be suppressed to a low level.

BRIEF DESCRIPTION OF THE DRAWINGS

The invention will be described with reference to the accompanying drawings, wherein like numbers reference like elements.

FIG. 5A is a schematic plan view showing a structure of an ultrasonic device, FIG. 5B is a schematic plan view showing the shape of an acoustic lens, and FIGS. 5C to 5E are schematic side cross-sectional views showing the shape of the acoustic lens.

DESCRIPTION OF EXEMPLARY EMBODIMENTS

Figure 1:
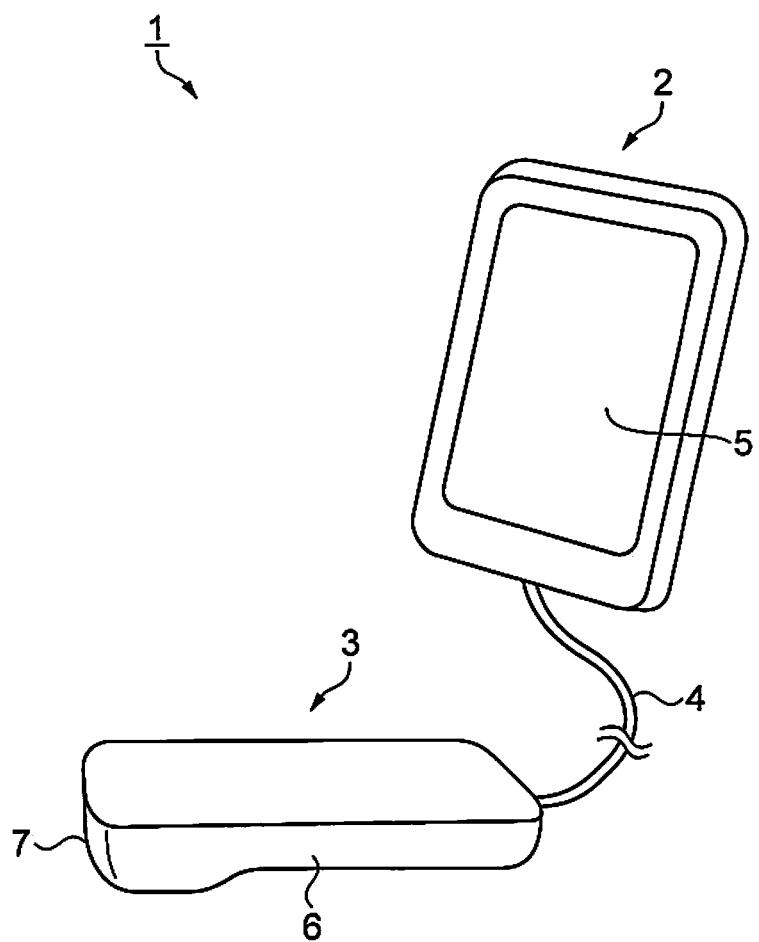
FIG. 1 is a schematic perspective view showing a configuration of an ultrasonic imaging apparatus according to a first embodiment.

In this embodiment, characteristic examples of an ultrasonic device and an ultrasonic imaging apparatus provided with the ultrasonic device will be described with reference to the drawings. It should be noted that the sizes of the members in the drawings are shown at different scales in each figure for perceptibility.

First Embodiment

Figure 2:
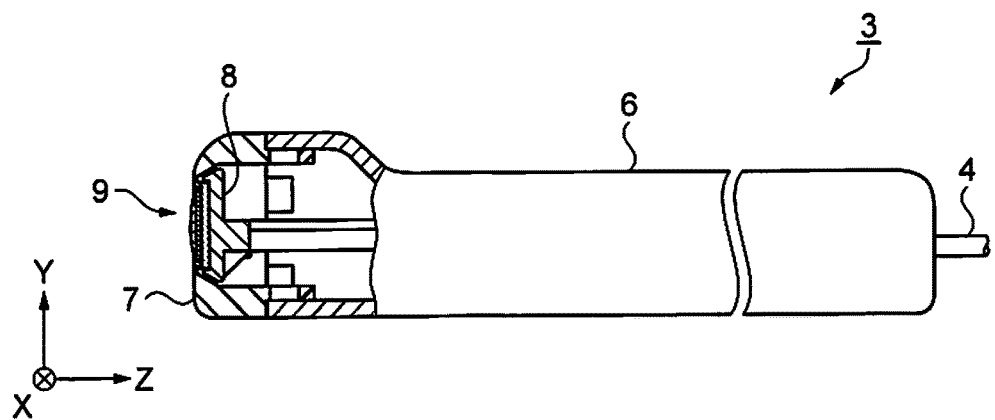
FIG. 2 is a schematic side cross-sectional view showing part of a structure of an ultrasonic probe.
Figure 3:
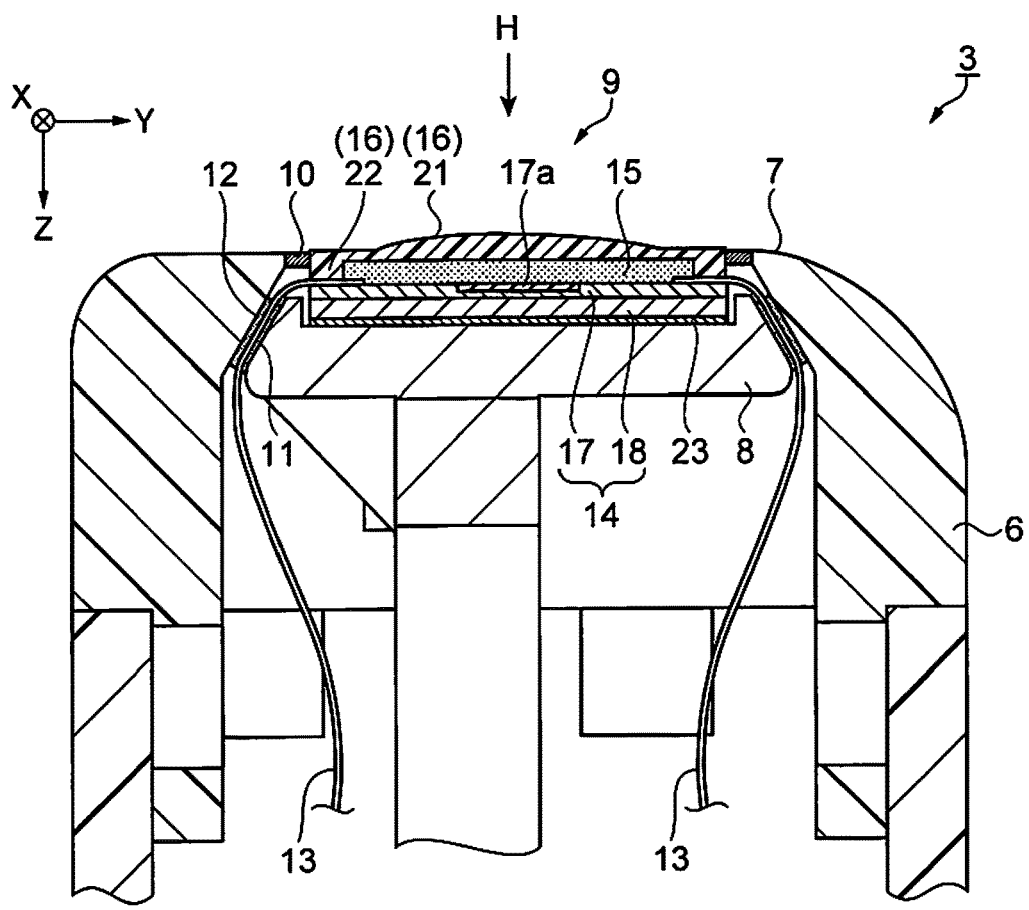
FIG. 3 is a schematic cross-sectional view showing a main part of the structure of the ultrasonic probe.

In this embodiment, an ultrasonic imaging apparatus for examining an interior portion of a human body will be described as an example of an electronic apparatus with reference to FIG. 1 to FIG. 8. FIG. 1 is a schematic perspective view showing a configuration of the ultrasonic imaging apparatus. FIG. 2 is a schematic side sectional view showing part of a structure of an ultrasonic probe. FIG. 3 is a schematic cross-sectional view showing a main part of the structure of the ultrasonic probe.

As shown in FIG. 1, an ultrasonic imaging apparatus 1 serving as an electronic apparatus includes an apparatus body 2 and an ultrasonic probe 3. The apparatus body 2 and the ultrasonic probe 3 are connected to each other by a cable 4. The apparatus body 2 and the ultrasonic probe 3 can exchange electrical signals via the cable 4. The apparatus body 2 incorporates a display unit 5 such as a display panel. The display unit 5 is a touch panel display, and serves also as a user interface unit with which an operator inputs information into the apparatus body 2. Hereinafter, the user interface unit will be referred to as "UI unit".

In the apparatus body 2, an image is generated on the basis of ultrasound detected by the ultrasonic probe 3, and the detection results that are output as an image are displayed on the screen of the display unit 5. The ultrasonic probe 3 includes a substantially rectangular parallelepiped housing 6. The cable 4 is connected to one end in the longitudinal direction of the housing 6. A head portion 7 that transmits and receives ultrasound is accommodated in the housing 6 located on the opposite side of the cable 4. The ultrasonic imaging apparatus 1 of this embodiment is configured so that the apparatus body 2 and the ultrasonic probe 3 are connected by the cable 4. However, the apparatus body 2 and the ultrasonic probe 3 may exchange signals wirelessly, without using the cable 4.

As shown in FIG. 2, the ultrasonic probe 3 includes an ultrasonic device 9 that is fixed to a support member 8 and that is accommodated within the housing 6. The ultrasonic device 9 is exposed from the head portion 7 of the housing 6 so that ultrasound is output from the ultrasonic device 9 to a target object. Further, the ultrasonic device 9 receives reflected waves of the ultrasound from the object. Such reflected waves are referred to also as echo waves. The housing 6 has a cylindrical shape, which is easy for the operator to grip. The ultrasonic device 9 is installed at one end of the housing 6, and the cable 4 is installed at the other end thereof. A direction extending from the ultrasonic device 9 toward the cable 4 is referred to as Z direction. Two directions orthogonal to the Z direction are referred to as X direction and Y direction. The ultrasonic device 9 substantially in the form of plates which extend in the X direction and the Y direction. The ultrasonic device 9 is longer in the X direction than in the Y direction.

As shown in FIG. 3, there is a gap between the ultrasonic device 9 and the head portion 7 of the housing 6. A sealing portion 10 filled with a silicone-based sealing material is provided in the gap. This sealing portion 10 prevents moisture and the like from entering the ultrasonic device 9. The support member 8 is located on the Z direction side of the ultrasonic device 9. A sealing structure is installed between the support member 8 and the head portion 7. This sealing structure includes an adhesive member 11 and an adhesive member 12. The adhesive member 11 is a member, such as a double-sided adhesive tape having elasticity, which is attached to the outer peripheral portion of the support member 8 of the ultrasonic device 9. The adhesive member 12 is a member, such as a double-sided adhesive tape having elasticity, which is attached to the housing 6.

Further, an FPC 13 (Flexible Printed Circuit) as a cable that connects the ultrasonic device 9 to a processing circuit is interposed in part of the sealing structure. The FPC 13 is fixed by being sandwiched by the adhesive member 11 and the adhesive member 12. The FPC 13 is referred to also as flexible printed circuit board. As the adhesive member 11 and the adhesive member 12, a double-sided adhesive tape formed by applying an acrylic-based adhesive material to a closed cell foam material such as polyethylene or urethane can be used, for example. In this way, a double sealing structure is employed for the ultrasonic probe 3, in which the sealing portion 10, the adhesive member 11, and the adhesive member 12 prevent moisture and the like from entering the housing 6.

The ultrasonic device 9 includes an ultrasonic element array substrate 14 serving as a substrate, an acoustic matching unit 15, an acoustic lens 16, and the FPC 13. The ultrasonic element array substrate 14 has an element substrate 17 and a back plate 18. The element substrate 17 is a substrate on which a plurality of ultrasonic elements 17a are arranged in an array, and has a rectangular shape elongated in the X direction, in plan view as viewed in the Z direction. The ultrasonic elements 17a need only transmit and receive ultrasound, and the form of the ultrasonic elements 17a is not specifically limited. The ultrasonic elements 17a may be PZT (lead zirconate titanate) in the form of thin films or PZT in the form of blocks, or may be elements configured to vibrate thin films using electrostatic force. In this embodiment, PZT thin films, for example, are used for the ultrasonic elements 17a.

The element substrate 17 is formed using a silicon substrate and has a thickness of about 150 μm to 200 μm. The back plate 18 having the same flat plate shape as the element substrate 17 is bonded to the opposite surface of the element-formed surface of the element substrate 17 oriented in the −Z direction. The back plate 18 serves to suppress excess vibration of the element substrate 17, for which a silicon substrate with a thickness of 500 μm to 600 μm is used. In addition to the silicon substrate, a metal plate may be used for the back plate 18. In the case where the influence of ultrasound that travels in the Z direction from the element substrate 17 is small, the ultrasonic device 9 may be formed without using the back plate 18.

On the surface of the element substrate 17 on which the ultrasonic elements are formed, a plurality of terminals connected to the plurality of ultrasonic elements are installed along the long sides extending in the X direction, in plan view. These terminals are connected to the terminals of the FPC 13, thus establishing electrical connection. The method for connecting the terminals of the ultrasonic elements to the terminals of the FPC 13 is not specifically limited. However, they are connected to each other, for example, via anisotropic conductive films in this embodiment.

On the surface of the element substrate 17 on which the ultrasonic elements are formed, the acoustic lens 16 having the same planar shape, as viewed in the −Z direction, as the ultrasonic element array substrate 14 is arranged. On a surface of the acoustic lens 16 in the −Z direction, a lens portion 21 that is convex in the thickness direction with a predetermined curvature is provided. On a surface thereof in the +Z direction, projecting portions 22, formed at the outer edge of the acoustic lens 16, protruding in the thickness direction are provided. The acoustic lens 16 is formed using a resin such as silicone resin. It is possible to adjust the acoustic impedance of the silicone resin by adding silica, or the like, to the silicone resin to change the specific gravity of the silicone resin.

The acoustic matching unit 15 is formed between the ultrasonic element array substrate 14 and the acoustic lens 16. For the acoustic matching unit 15, a silicone-based adhesive agent is used. Curing of the adhesive agent causes the ultrasonic element array substrate 14 and the acoustic lens 16 to be secured (bonded) to each other. The thus cured adhesive agent (resin) functions as the acoustic matching unit 15.

The acoustic lens 16 serves to guide ultrasound transmitted from the ultrasonic elements of the element substrate 17 efficiently to a target object, and also to guide echo waves reflected back from the object efficiently to the ultrasonic elements. The acoustic matching unit 15 serves to relax the acoustic impedance mismatch between the acoustic lens 16 and the ultrasonic elements. The back plate 18 of the ultrasonic device 9 is fixed to the support member 8 by an adhesive agent 23.

Figure 4:
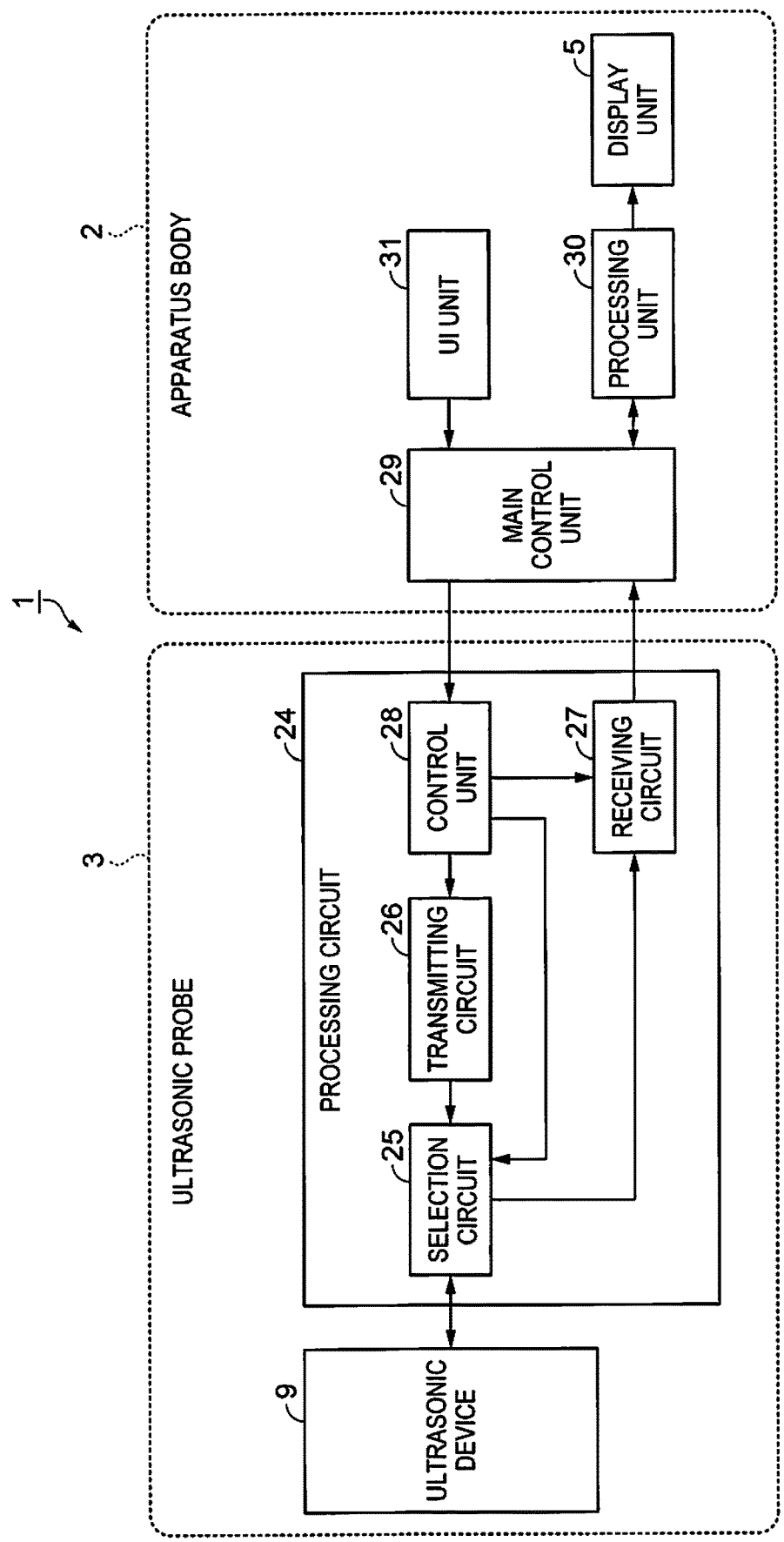
FIG. 4 is a block diagram illustrating the control of the ultrasonic imaging apparatus.

FIG. 4 is a block diagram illustrating the control of the ultrasonic imaging apparatus. As shown in FIG. 4, the ultrasonic imaging apparatus includes the apparatus body 2 and the ultrasonic probe 3. The ultrasonic probe 3 includes the ultrasonic device 9 and a processing circuit 24 as a driving circuit. The processing circuit 24 has a selection circuit 25, a transmitting circuit 26, a receiving circuit 27, and a control unit 28. This processing circuit 24 performs transmission processing and reception processing for the ultrasonic device 9.

The transmitting circuit 26 outputs transmission signals VT to the ultrasonic device 9 via the selection circuit 25 in a transmission period. Specifically, the transmitting circuit 26 generates the transmission signals VT, on the basis of control by the control unit 28, and outputs them to the selection circuit 25. Then, the selection circuit 25 outputs the transmission signals VT from the transmitting circuit 26, on the basis of control by the control unit 28. The frequency and amplitude voltage of the transmission signals VT are set by the control unit 28.

The receiving circuit 27 performs reception processing to receive reception signals VR from the ultrasonic device 9. Specifically, the receiving circuit 27 receives the reception signals VR from the ultrasonic device 9 via the selection circuit 25 in a reception period. The receiving circuit 27 performs reception processing such as amplification of the reception signals, gain setting, frequency setting, and A/D conversion (analog/digital conversion). The receiving circuit 27 outputs the results of the reception processing to the apparatus body 2 as detected data (detected information). The receiving circuit 27, for example, can be composed of a low-noise amplifier, a voltage-controlled attenuator, a programmable gain amplifier, a low-pass filter, an A/D converter, and the like.

The control unit 28 controls the transmitting circuit 26 and the receiving circuit 27. Specifically, the control unit 28 controls the transmitting circuit 26 for generation of the transmission signals VT and output processing, and controls the receiving circuit 27 for frequency setting of the reception signals VR, gain, or the like. The selection circuit 25 outputs the selected transmission signals VT to the ultrasonic device 9, on the basis of control by the control unit 28.

The apparatus body 2 includes the display unit 5, a main control unit 29, a processing unit 30, and a UI unit 31 (user interface unit). The main control unit 29 controls the ultrasonic probe 3 for transmission and reception of ultrasound, and controls the processing unit 30 for image processing of detected data, for example. The processing unit 30 receives detected data from the receiving circuit 27, and performs image processing to remove noises, generation of image data to be displayed, or the like. The UI unit 31 outputs necessary instruction (command) to the main control unit 29 on the basis of operation (such as touch panel operation) by the user. The display unit 5, for example, is a liquid crystal display, and displays the image data to be displayed received from the processing unit 30. It should be noted that part of control by the main control unit 29 may be performed by the control unit 28 of the processing circuit 24, or part of control by the control unit 28 may be performed by the main control unit 29.

FIG. 5A is a schematic plan view showing a structure of the ultrasonic device, as viewed in the direction of the arrow H in the ultrasonic probe 3 of FIG. 3. As shown in FIG. 5A, the ultrasonic device 9 has a rectangular shape elongated in the X direction as viewed in the H direction. The FPC 13 is connected to the ultrasonic device 9 in the Y direction and the −Y direction. The FPC 13 has a strip shape with a large width in the X direction of the drawing. The acoustic matching unit 15 is discretely protruding in the periphery of the ultrasonic device 9.

FIG. 5B is a schematic plan view showing the shape of the acoustic lens, as viewed in the −Z direction. FIG. 5C to FIG. 5E are schematic side cross-sectional views showing the shape of the acoustic lens. FIG. 5C is a schematic side cross-sectional view taken along the line A-A in FIG. 5B. FIG. 5D is a schematic side cross-sectional view taken along the line B-B in FIG. 5B. FIG. 5E is a schematic side cross-sectional view taken along the line C-C in FIG. 5B.

As shown in FIG. 5B, the acoustic lens 16 has the projecting portions 22 installed along its outer perimeter. The projecting portions 22 are installed in the places opposed to the FPC 13 and in the places not opposed to the FPC 13. The openings between adjacent projecting portions 22 that are located in the places opposed to the FPC 13 are referred to as first openings 32. The openings between adjacent projecting portions 22 that are located in the places not opposed to the FPC 13 are referred to as second openings 33.

The first openings 32 are longer than the second openings 33. The ratio of the first openings 32 per unit length in the outer perimeter of the acoustic lens 16 is higher than that of the second openings 33. In other words, the projecting portions 22 are provided at a lower ratio per unit length in the places where the FPC 13 is installed than in the places where the FPC 13 is not installed.

In the +Y direction and in the −Y direction, the FPC 13 is interposed between the ultrasonic element array substrate 14 and the projecting portions 22 of the acoustic lens 16. Such places are referred to as first places. In the +X direction and in the −X direction, the projecting portions 22 of the acoustic lens 16 are directly in contact with the ultrasonic element array substrate 14, without the FPC 13 being interposed. Such places are referred to as second places. The projected length of the projecting portions 22 per unit length in the direction along the outer perimeter of the ultrasonic element array substrate 14 is larger in the second places than in the first places.

As shown in FIG. 5C, the length of the projecting portions 22 in the Z direction in the places opposed to the FPC 13 is taken as a first projecting length 22a. As shown in FIG. 5D, the projecting portions 22 are not installed in the first openings 32. As shown in FIG. 5E, the length of the projecting portions 22 in the Z direction in the places not opposed to the FPC 13 is taken as a second projecting length 22b. The first projecting length 22a and the second projecting length 22b are not specifically limited. However, in this embodiment, the first projecting length 22a is 30 μm to 50 μm, and the second projecting length 22b is 100 μm to 110 μm, for example. The thickness of the FPC 13 in the Z direction is 50 μm to 70 μm. The sum of the thickness of the FPC 13 in the Z direction and the first projecting length 22a is set to be smaller than the second projecting length 22b.

Figure 6:
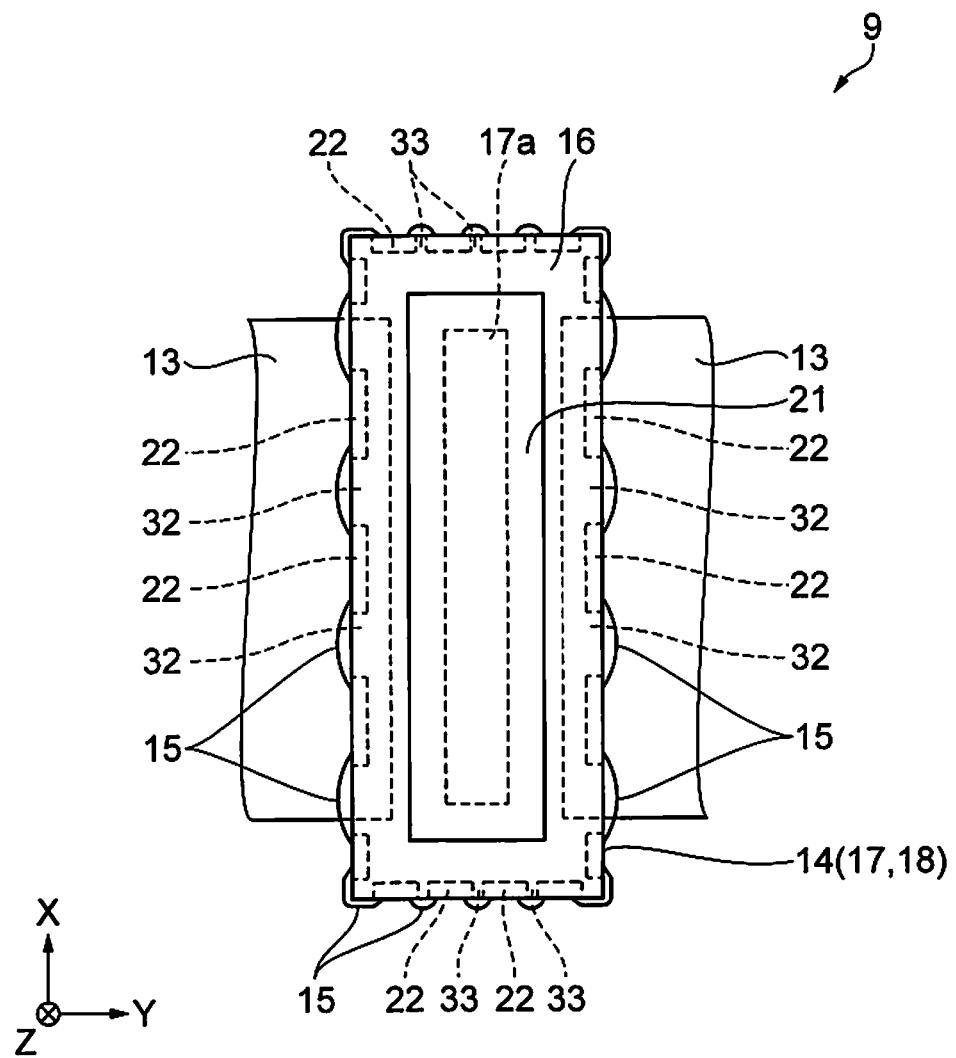
FIG. 6 is a schematic plan view showing the structure of the ultrasonic device.

FIG. 6 is a schematic plan view showing the structure of the ultrasonic device. As shown in FIG. 6, the acoustic matching unit 15 protrudes in the periphery of the acoustic lens 16 through the first openings 32 and the second openings 33. Since the first openings 32 are longer than the second openings 33, the acoustic matching unit 15 protrudes more from the first openings 32 than from the second openings 33.

Figure 7A:
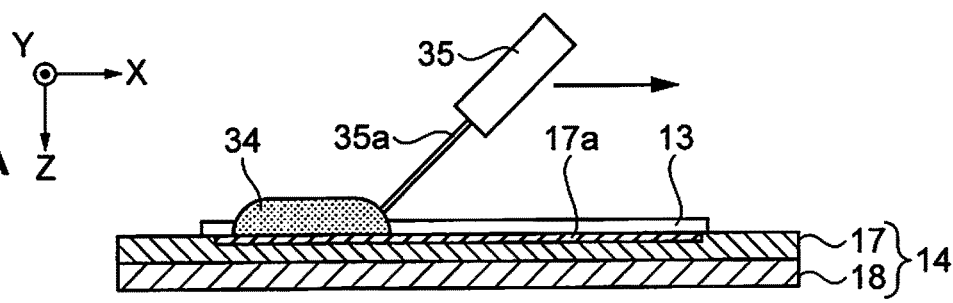
FIGS. 7A to 7D are schematic diagrams for describing a method for manufacturing the ultrasonic device.
Figure 7B:
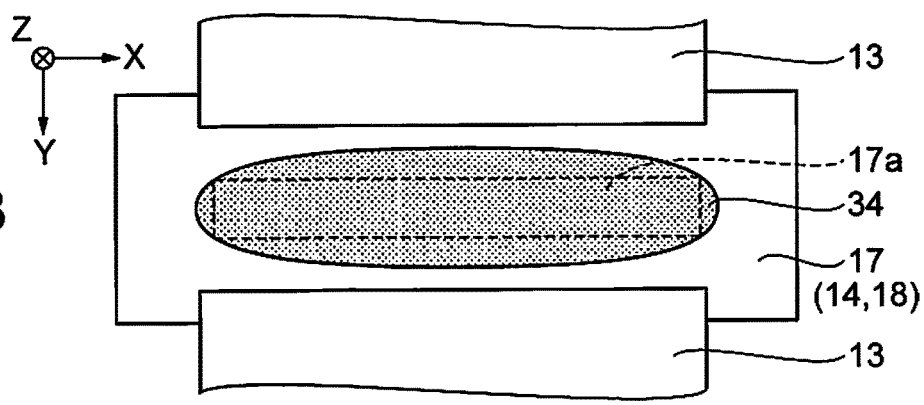

Next, a method for manufacturing the ultrasonic device 9 will be described. FIGS. 7A to 7D and FIGS. 8A to 8D are schematic diagrams for describing the method for manufacturing the ultrasonic device. As shown in FIG. 7A and FIG. 7B, the element substrate 17 on which the ultrasonic elements are installed is first prepared. The method for forming the ultrasonic elements is known to the public, and thus the specific description thereof is omitted. The ultrasonic elements are formed by repeating film formation by sputtering, vapor deposition, or the like, and a photolithographic process. An adhesive agent is then applied to the element substrate 17 or the back plate 18, and the element substrate 17 and the back plate 18 are laminated together. Next, the adhesive agent is solidified by heating and drying. Thus, the ultrasonic element array substrate 14 is completed.

Next, the FPC 13 is connected to the ultrasonic element array substrate 14. In the FPC 13, terminals are arrayed at the ends of the lines. Further, terminals are formed on the element substrate 17 at the same spacing as the pitch of the terminals of the FPC 13. An anisotropic conductive film is arranged between the element substrate 17 and the FPC 13. Subsequently, the terminals of the FPC 13 and the terminals of the element substrate 17 are opposed to each other, followed by heating, thereby allowing the FPC 13 to be mounted on the element substrate 17. Other than that, the FPC 13 may be mounted on the element substrate 17 by soldering the terminals of the FPC 13 and the terminals of the element substrate 17, or may be mounted with the resin core bump being interposed therebetween.

An adhesive agent 34 is applied at the center of the surface of the element substrate 17 on the −Z direction side as a resin. The adhesive agent 34 can be applied using a syringe 35. The inside of the syringe 35 is loaded with the adhesive agent 34, and the adhesive agent 34 is pressed by compressed air, thereby flowing out through a needle part 35a. The pattern in which the needle part 35a is moved is not specifically limited. However, application can be performed in a spiral pattern. Immediately after flowing out, the adhesive agent 34 is viscous and forms one substantially elliptical shape due to the action of surface tension. Other than that, the adhesive agent 34 may be applied by printing such as screen printing.

The adhesive agent 34 is a material that serves as the acoustic matching unit 15 after solidification. The adhesive agent 34 is not specifically limited, but single-component room-temperature-curable silicone-rubber-based adhesive agents can be used favorably. After being cured, silicone rubber exhibits superior heat resistance, cold resistance, and electrical insulating properties, and therefore it can be used as an acoustic impedance without any problems. Further, silicone rubber can be cured by controlling moisture in the air. Other than that, photocurable adhesive agents can be used. Since their curing time is short, the acoustic lens 16 can be bonded to the element substrate 17 with good productivity.

Figure 7C:
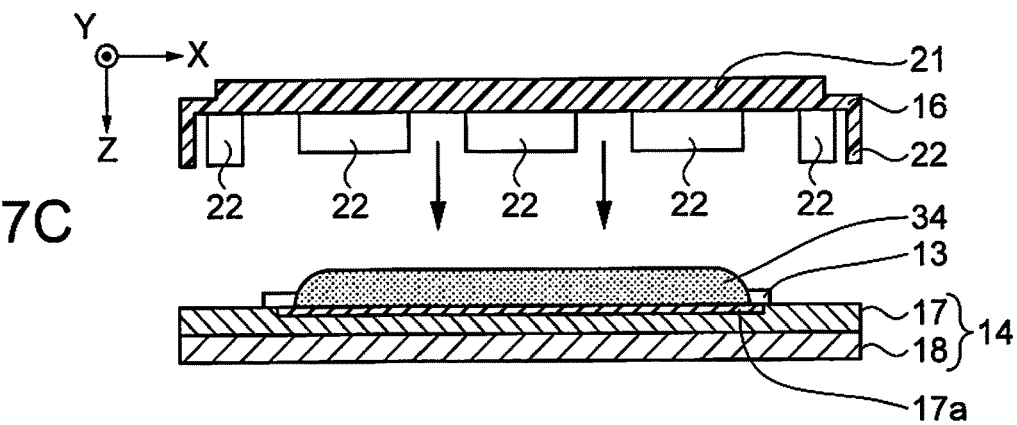
Figure 7D:
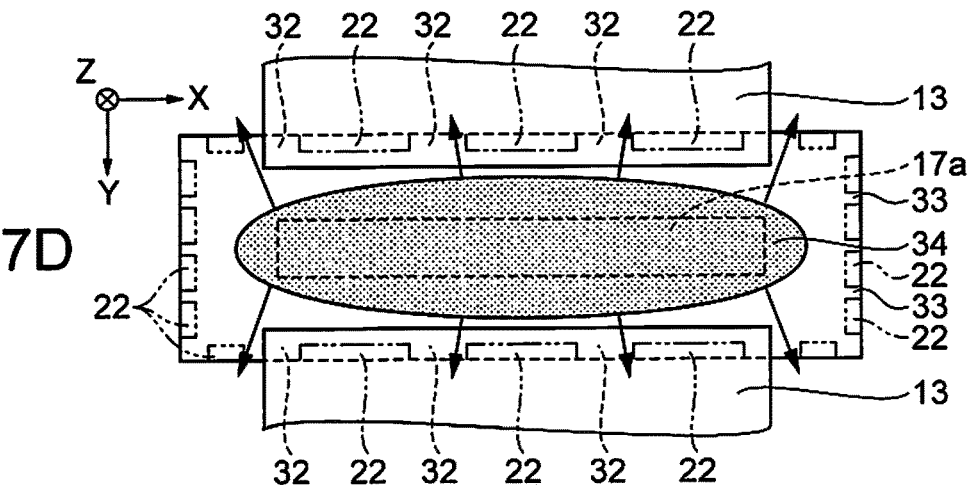
Figure 8A:
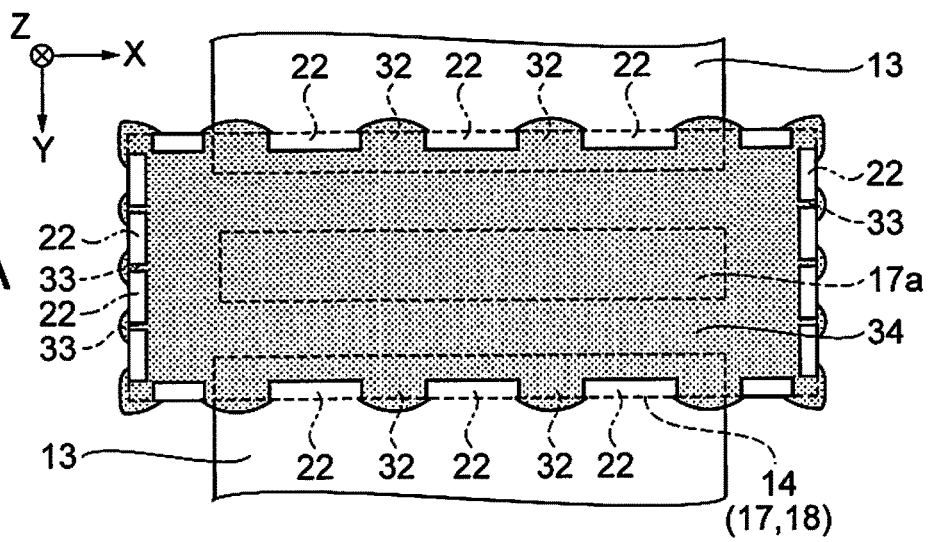
FIGS. 8A to 8D are schematic diagrams for describing the method for manufacturing the ultrasonic device.

As shown in FIG. 7C, the adhesive agent 34 sandwiched by the ultrasonic element array substrate 14 and the acoustic lens 16 is pressed. As shown in FIG. 7D, the adhesive agent 34 is pressed and flows so as to spread toward the outer perimeters of the ultrasonic element array substrate 14 and the acoustic lens 16. After the adhesive agent 34 has reached the projecting portions 22, the adhesive agent 34 flows, mainly passing through the first openings 32 and the second openings 33. As a result, as shown in FIG. 8A, the adhesive agent 34 protrudes through the first openings 32 and the second openings 33 from the outer perimeters of the ultrasonic element array substrate 14 and the acoustic lens 16.

The projecting portions 22 extend along the outer perimeter of the ultrasonic element array substrate 14. The projecting portions 22 are provided at a lower ratio per unit length in the places where the FPC 13 is installed than in the places where the FPC 13 is not installed. Further, the first openings 32 located in the places where the FPC 13 is present are longer than the second openings 33 located in the places where the FPC 13 is not present. This makes it easy for the adhesive agent 34 to swiftly flow out to the places where the FPC 13 is present. Due to the swiftness when the adhesive agent 34 flows through the first openings 32, the air in the periphery of the FPC 13 can be pushed out. Accordingly, air bubbles can be pushed out without remaining in the junction between the FPC 13 and the ultrasonic element array substrate 14.

In the case where air bubbles remain, the thickness of the adhesive agent 34 decreases in the places where the air bubbles are formed. Therefore, the moisture permeability increases, which may possibly cause current leakage due to the electrolytic corrosion between the terminals. Further, in the case where the moisture permeability increases, the adhesive agent 34 easily separates due to the moisture. This weakens the bonding strength between the ultrasonic element array substrate 14 and the acoustic lens 16. In the acoustic lens 16, the width of the first openings 32 is larger than that of the second openings 33, and therefore the first openings 32 can be reliably filled with the adhesive agent 34.

Further, due to the swiftness when the adhesive agent 34 flows through the first openings 32, the filling with the adhesive agent 34 is sufficient. Accordingly, a reduction in thickness of the adhesive agent 34 and an increase in moisture permeability due to insufficient filling can be suppressed.

Figure 8B:
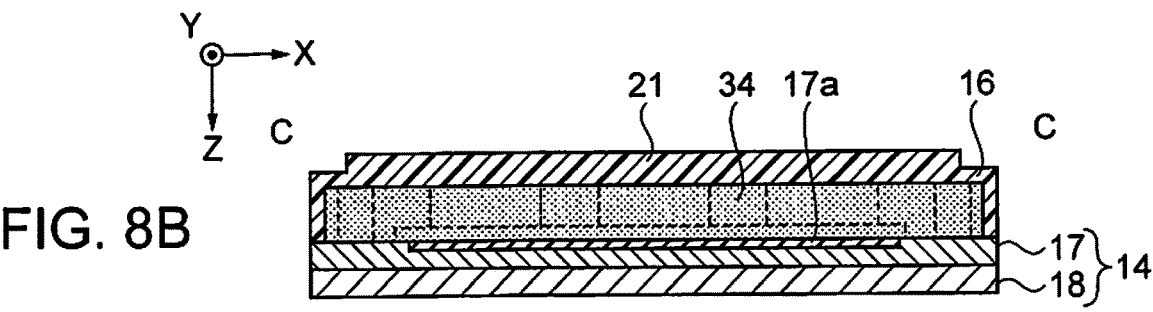
Figure 8C:
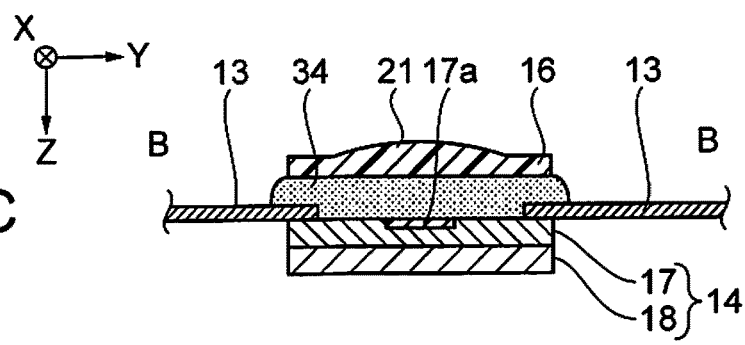
Figure 8D:
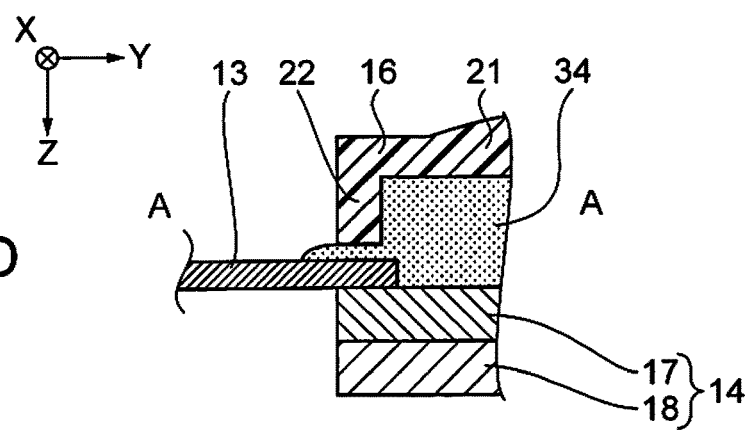

FIG. 8B is a schematic side cross-sectional view taken along the line C-C shown in FIG. 5B. As shown in FIG. 8B, the place sandwiched by the ultrasonic element array substrate 14 and the acoustic lens 16 is filled with the adhesive agent 34. Thus, the places where the FPC 13 is joined to the element substrate 17 are covered by the adhesive agent 34. FIG. 8C is a schematic side cross-sectional view taken along the line B-B shown in FIG. 5B. As shown in FIG. 8C, the adhesive agent 34 flows on the FPC 13 at the first openings 32. Accordingly, the FPC 13 is reliably covered by the adhesive agent 34. FIG. 8D is a schematic side cross-sectional view taken along the line A-AA shown in FIG. 5B. As shown in FIG. 8D, gaps are formed between the FPC 13 and the projecting portions 22. The adhesive agent 34 flows out through the gaps between the FPC 13 and the projecting portions 22 onto the FPC 13. Accordingly, the FPC 13 is reliably covered by the adhesive agent 34.

The adhesive agent 34 is heated and dried, so as to serve as the acoustic matching unit 15. As the adhesive agent 34, a material that solidifies by reaction with light may be employed, or a material that solidifies by reaction with moisture may be employed. A material in a form that is easy to manufacture can be selected. By performing the aforementioned steps, the ultrasonic device 9 is completed.

As described above, this embodiment has the following effects.

(1) According to this embodiment, the projecting portions 22 extend along the outer perimeter of the ultrasonic element array substrate 14. The projecting portions 22 are provided at a lower ratio per unit length in the places where the FPC 13 is installed than in the places where the FPC 13 is not installed. Thus, the first openings 32 located in the places where the FPC 13 is present are longer than the second openings 33 located in the places where the FPC 13 is not present.

This makes it easier for the adhesive agent 34 to swiftly flow out to the places where the FPC 13 is present than to the places where the FPC 13 is not present. Then, the adhesive agent 34, in which formation of air bubbles is suppressed, is solidified. As a result, the acoustic matching unit 15 in which formation of air bubbles is suppressed covers the FPC 13, and therefore the moisture permeability of the junction between the element substrate 17 and the FPC 13 can be suppressed to a low level.

(2) According to this embodiment, the acoustic matching unit 15 is partially located between the FPC 13 and the projecting portions 22. This allows the areas between the FPC 13 and the projecting portions 22 to be covered by the acoustic matching unit 15 as well. Accordingly, the moisture permeability can be suppressed to a low level.

(3) According to this embodiment, the ultrasonic probe 3 includes the ultrasonic device 9 in which the moisture permeability of the junction between the FPC 13 and the element substrate 17 is suppressed to a low level. Accordingly, the ultrasonic probe 3 allows transmission and reception of ultrasound to be performed with high long-term reliability.

(4) According to this embodiment, the ultrasonic imaging apparatus 1 includes the ultrasonic device 9 and the processing unit 30. The processing unit 30 generates image data using the output of the ultrasonic device 9. The ultrasonic imaging apparatus 1 includes the ultrasonic device 9 in which the moisture permeability of the junction between the FPC 13 and the element substrate 17 is suppressed to a low level. Accordingly, it is possible to provide the ultrasonic imaging apparatus 1, which allows transmission and reception of ultrasound to be performed with high long-term reliability.

Second Embodiment

Next, an embodiment of the ultrasonic device will be described with reference to FIG. 9, which is a schematic plan view showing the structure of the ultrasonic device. This embodiment is different from the first embodiment in that the projecting portions 22 and the first openings 32 having shapes different from those shown in FIG. 6 are employed. It should be noted that descriptions for the same parts as in the first embodiment are omitted.

Figure 9:
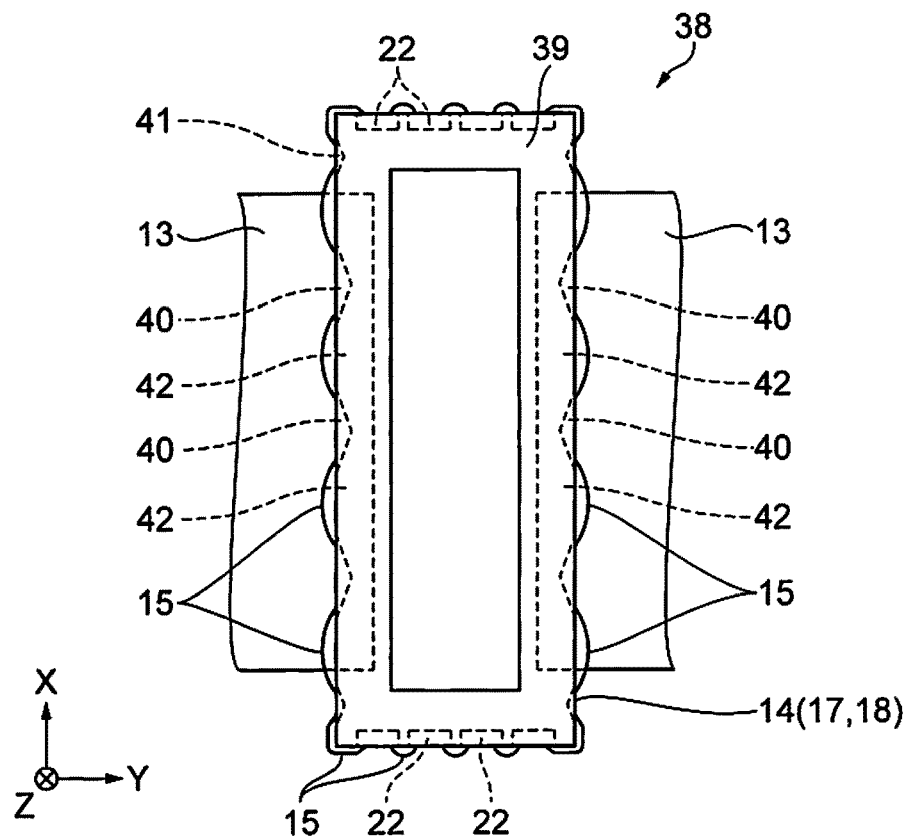
FIG. 9 is a schematic plan view showing a structure of an ultrasonic device according to a second embodiment.

That is, as shown in FIG. 9, an ultrasonic device 38 includes an acoustic lens 39 in this embodiment. In the acoustic lens 39, the projecting portions 22 are installed on the +X direction side and the −X direction side, and projecting portions 40 and projecting portions 41 are installed on the +Y direction side and the −Y direction side. The projecting portions 40 are installed in the places opposed to the FPC 13, and the projecting portions 41 are installed in the places not opposed to the FPC 13. The projecting portions 40 and the projecting portions 41 are triangular, and have one of the vertex angles arranged inside the acoustic lens 39. In other words, in plan view as viewed in the thickness direction of the ultrasonic element array substrate 14, the length of the cross sections of the projecting portions 40 along the outer perimeter direction of the ultrasonic element array substrate 14 is smaller at positions on the inner side than on the outer peripheral side of the ultrasonic element array substrate 14. Further, first openings 42 serving as openings between the projecting portions 40 are longer at positions on the inner side than on the outer peripheral side. This can reduce the fluid resistance of the adhesive agent 34 passing through the first openings 42, and therefore the adhesive agent 34 can swiftly flow out toward the outside of the acoustic lens 39.

Third Embodiment

Next, an embodiment of the ultrasonic device will be described with reference to FIG. 10, which is a schematic plan view showing the structure of the ultrasonic device. This embodiment is different from the second embodiment in that the projecting portions 40 and the first openings 42 are arranged differently from those shown in FIG. 9. It should be noted that descriptions for the same parts as in the second embodiment are omitted.

Figure 10:
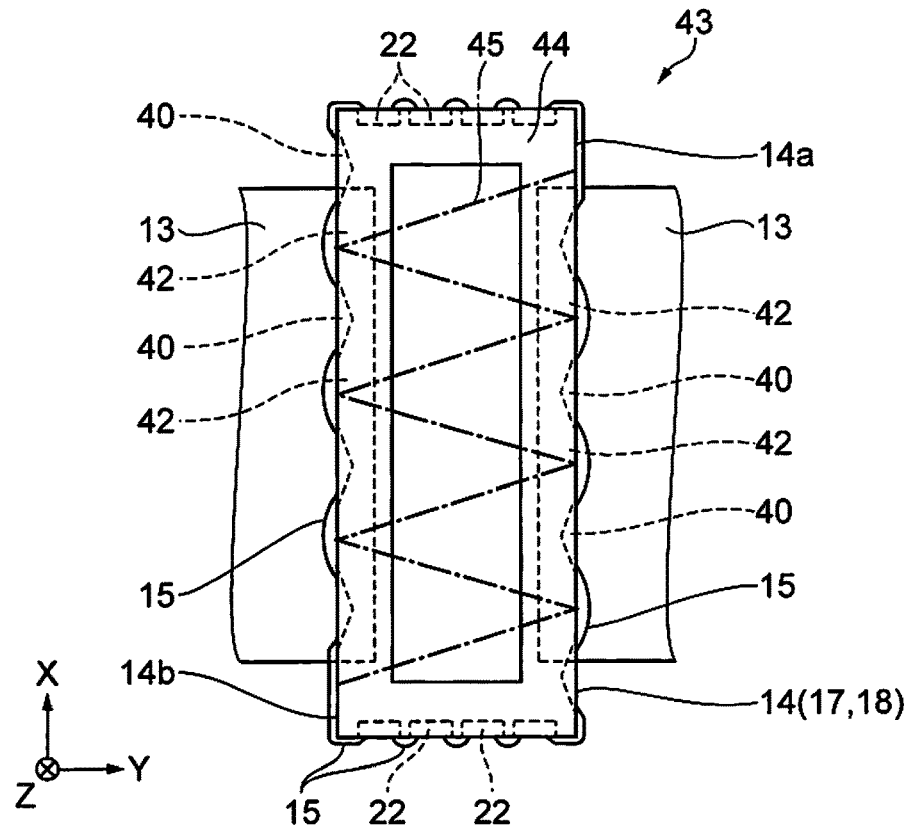
FIG. 10 is a schematic plan view showing a structure of an ultrasonic device according to a third embodiment.

That is, as shown in FIG. 10, an ultrasonic device 43 includes an acoustic lens 44 in this embodiment. In the acoustic lens 44, the projecting portions 40 are installed on the +Y direction side and the −Y direction side. The side of the ultrasonic element array substrate 14 on the +Y direction side as viewed in the Z direction is referred to as first side 14a, and the side thereof on the −Y direction side is referred to as second side 14b. The FPC 13 is located on the first side 14a and the second side 14b. Further, the first openings 42 on the first side 14a and the first openings 42 on the second side 14b are arranged alternatingly in the X direction.

In the case where the first openings 42 on the first side 14a and the first openings 42 on the second side 14b are located in the places opposed to each other, lines connecting the opposed first openings 42 are parallel to each other. Then, the acoustic lens 44 easily bends along the parallel lines because there is less strength in the places where the first openings 42 are present than in the places where the projecting portions 40 are present. On the other hand, in the case where the first openings 42 are arranged alternatingly, lines 45 connecting the first openings 42 on the first side 14a and the first openings 42 on the second side 14b intersect each other. Accordingly, in the acoustic lens 44, the places susceptible to bending extend along the intersecting lines 45, and therefore the acoustic lens 44 can be made less likely to bend as compared to the case where the places susceptible to bending extend along parallel lines.

Fourth Embodiment

Next, an embodiment of the ultrasonic imaging apparatus will be described with reference to FIG. 11, which is a schematic perspective view showing the configuration of the ultrasonic imaging apparatus. In the ultrasonic imaging apparatus of this embodiment, the ultrasonic device 9 of the first embodiment is installed. It should be noted that descriptions for the same parts as in the first embodiment are omitted.

Figure 11:
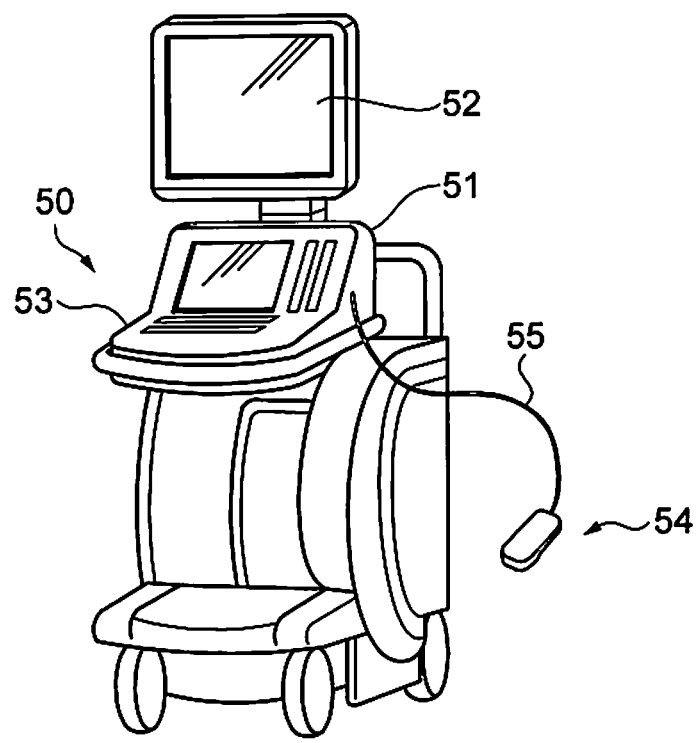
FIG. 11 is a schematic perspective view showing a configuration of an ultrasonic imaging apparatus according to a fourth embodiment.

As shown in FIG. 11, an ultrasonic imaging apparatus 50 serving as an electronic apparatus is a stationary ultrasonic imaging apparatus. The ultrasonic imaging apparatus 50 has an apparatus body 51 (electronic apparatus body), a display unit 52 that displays image data to be displayed, a processing unit 53 that forms an image, an ultrasonic probe 54, and a cable 55. The ultrasonic device 9 is installed in the ultrasonic probe 54, and the processing unit 53 generates an image using an output of the ultrasonic device 9. The display unit 52 displays the image generated by the processing unit 53.

The ultrasonic imaging apparatus 50 can be used for the in-vivo measurement of fat thickness, muscle thickness, bloodstream, bone density, or the like. The ultrasonic device 9 included in the ultrasonic imaging apparatus 50, in which the moisture permeability of the junction between the FPC 13 and the ultrasonic element array substrate 14 is suppressed to a low level, allows transmission and reception of ultrasound to be performed with high long-term reliability. Accordingly, it can be said that the ultrasonic imaging apparatus 50 is an apparatus including the ultrasonic device 9 which allows transmission and reception of ultrasound to be performed with good reliability over a long period of time.

The invention is not limited to the foregoing embodiments. The specific arrangements and procedures in practicing the invention may be altered by another arrangement or the like as necessary as long as the objects of the invention can be achieved. Many modifications can be made by a person of ordinary skill in the art without departing from the technical scope of the invention. Examples of the modifications will be described below.

Modification 1

In the first embodiment, the FPC 13 is directly connected to the element substrate 17. The FPC 13 may be connected to the element substrate 17 by wire bonding. In the case where the density of the ultrasonic elements 17a of the element substrate 17 is high and the size of the element substrate 17 is small, the terminals of the FPC 13 can be easily connected to the terminals of the element substrate 17 by using wires.

Modification 2

In the first embodiment, the second openings 33 are installed on the shorter sides the ultrasonic device 9. In the case where the viscosity of the adhesive agent 34 is low so that the adhesive agent 34 easily flows, the second openings 33 may be omitted. The shape of the acoustic lens 16 is simplified by omitting the second openings 33, which facilitates manufacturing.

Modification 3

In the first embodiment, the FPC 13 is installed on the two sides in the +Y direction and the −Y direction. The FPC 13 may be installed on one side, or on three sides. Also in such cases, the adhesive agent 34 is allowed to flow with good fluidity by setting the length of the first openings 32 in the places where the FPC 13 is installed to be larger than that of the second openings 33. As a result, it is possible to reduce residual air bubbles and suppress the moisture permeability in the electrodes of the FPC 13 to a low level.

Modification 4

In the first embodiment, the ultrasonic device 9 has a quadrangular shape. However, the ultrasonic device 9 may have a triangular or polygon shape, or a shape including a circular arc. It is also possible to employ a shape suitable for the arrangement of the ultrasonic elements.

Modification 5

In the second embodiment, the shape of the projecting portions 40 as viewed in the Z direction is triangular. The shape of the projecting portions 40 as viewed in the Z direction may be semicircular or trapezoidal. Such shapes also allow the first openings 42 to be wider on the inner sides than on the outer sides, and therefore the fluid resistance when the adhesive agent 34 flows can be reduced.

The entire disclosure of Japanese Patent Application No. 2014-000132 filed on Jan. 6, 2014 is expressly incorporated by reference herein.

What is claimed is:

1. An ultrasonic device comprising:
a substrate including ultrasonic elements configured to transmit and receive ultrasound;
a cable electrically connected to the ultrasonic elements and mounted on the substrate:
an acoustic lens having a plurality of projecting portions projecting toward the substrate, the plurality of projecting portions each having an end surface facing one of the substrate and the cable and connected to the one of the substrate and the cable; and
an acoustic matching unit located between the substrate and the acoustic lens, wherein the plurality of projecting portions are aligned along an outer perimeter of the substrate, and
a ratio of a total length of the plurality of projecting portions provided in a place where the cable is installed with respect to a total length of the outer perimeter of the substrate where the cable is installed is lower than a ratio of a total length of the plurality of projecting portions provided in a place where the cable is not installed with respect to a total length of the outer perimeter of the substrate where the cable is not installed.

2. The ultrasonic device according to claim 1, wherein the plurality of projecting portions are provided with intervals therebetween, and lengths of the intervals between the plurality of projecting portions provided in the place where the cable is installed along the outer perimeter of the substrate is larger than lengths of the intervals between the plurality of projecting portions provided in the place where the cable is not installed.

3. An ultrasonic probe comprising:
the ultrasonic device according to claim 2; and
a driving circuit configured to drive the ultrasonic device.

4. An electronic apparatus comprising:
the ultrasonic device according to claim 2;
a processing unit connected to the ultrasonic device, the processing unit being configured to perform processing to generate an image using an output of the ultrasonic device; and
a display unit configured to display the image.

5. The ultrasonic device according to claim 1, wherein the plurality of projecting portions have a smaller length, in a direction along the outer perimeter of the substrate, at positions on an inner side than on an outer peripheral side of the substrate.

6. An ultrasonic probe comprising:
the ultrasonic device according to claim 5; and
a driving circuit configured to drive the ultrasonic device.

7. An electronic apparatus comprising:
the ultrasonic device according to claim 5;
a processing unit connected to the ultrasonic device, the processing unit being configured to perform processing to generate an image using an output of the ultrasonic device; and
a display unit configured to display the image.

8. The ultrasonic device according to claim 1, wherein the substrate has a first side and a second side that are opposed to each other, the cable overlaps the first side and the second side, and openings between the plurality of projecting portions on the first side and openings between the plurality of projecting portions on the second side are arranged alternatingly.

9. An ultrasonic probe comprising:
the ultrasonic device according to claim 8; and
a driving circuit configured to drive the ultrasonic device.

10. An electronic apparatus comprising:
the ultrasonic device according to claim 8;
a processing unit connected to the ultrasonic device, the processing unit being configured to perform processing to generate an image using an output of the ultrasonic device; and
a display unit configured to display the image.

11. The ultrasonic device according to claim 1, wherein the acoustic matching unit is partially located between the cable and the plurality of projecting portions.

12. An ultrasonic probe comprising:
the ultrasonic device according to claim 11; and
a driving circuit configured to drive the ultrasonic device.

13. An electronic apparatus comprising:
the ultrasonic device according to claim 11;
a processing unit connected to the ultrasonic device, the processing unit being configured to perform processing to generate an image using an output of the ultrasonic device; and
a display unit configured to display the image.

14. An ultrasonic probe comprising:
the ultrasonic device according to claim 1; and
a driving circuit configured to drive the ultrasonic device.

15. An electronic apparatus comprising:
the ultrasonic device according to claim 1;
a processing unit connected to the ultrasonic device, the processing unit being configured to perform processing to generate an image using an output of the ultrasonic device; and
a display unit configured to display the image.

16. The ultrasonic device according to claim 1, wherein the substrate has a flat plate shape with a main surface of the substrate being parallel to an alignment direction of the ultrasonic elements.

17. The ultrasonic device according to claim 1, wherein the cable is a flexible printed circuit.

18. The ultrasonic device according to claim 1, wherein the acoustic lens and the projecting portions are formed as a one-piece, unitary member.

* * * * *